(12) United States Patent
Chen et al.

(10) Patent No.: US 7,964,024 B2
(45) Date of Patent: Jun. 21, 2011

(54) APPARATUS FOR INSTALLING OR UNINSTALLING CARBON DIOXIDE ABSORBENT CANISTER

(75) Inventors: Peitao Chen, Shenzhen (CN); Kun Cai, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 349 days.

(21) Appl. No.: 12/201,747

(22) Filed: Aug. 29, 2008

(65) Prior Publication Data

US 2009/0056720 A1 Mar. 5, 2009

(30) Foreign Application Priority Data

Aug. 31, 2007 (CN) .......................... 2007 1 0076832

(51) Int. Cl.
*A61M 16/01* (2006.01)
*B01D 53/02* (2006.01)

(52) U.S. Cl. ... 95/139; 96/147; 128/202.27; 128/205.28

(58) Field of Classification Search ............. 128/202.27, 128/205.12, 205.24, 205.27; 96/108, 147, 96/151; 55/506; 210/282, 236; 95/139
See application file for complete search history.

(56) References Cited

U.S. PATENT DOCUMENTS

| | | | |
|---|---|---|---|
| 2,693,181 A | | 11/1954 | Hamilton |
| 3,589,870 A | * | 6/1971 | Rankin .......................... 422/122 |
| 5,230,795 A | * | 7/1993 | Yang .............................. 210/236 |
| 5,744,030 A | * | 4/1998 | Reid et al. ..................... 210/235 |
| 6,397,839 B1 | | 6/2002 | Stradella |
| 7,138,053 B2 | * | 11/2006 | Sato .............................. 210/232 |
| 2009/0107505 A1 | * | 4/2009 | Kleinschmidt ........... 128/205.28 |

FOREIGN PATENT DOCUMENTS

| | | |
|---|---|---|
| CA | 2041184 | 11/1991 |
| CN | 2270970 Y | 12/1997 |
| CN | 2331369 Y | 8/1999 |
| CN | 2621235 Y | 6/2004 |
| DE | 4108383 | 9/1992 |
| DE | 10014829 B4 | 4/2006 |
| EP | 1712246 A1 | 10/2006 |

(Continued)

OTHER PUBLICATIONS

Machine generated English translation of JP 11-342206, published Dec. 1999.*
Chinese International Search Report dated Jun. 12, 2008 for China Patent Application No. 200710076832.1.

(Continued)

*Primary Examiner* — Frank M Lawrence
(74) *Attorney, Agent, or Firm* — Vista IP Law Group, LLP

(57) ABSTRACT

Disclosed is an apparatus for installing a carbon dioxide absorbent canister which comprises a body, a lifting member, and a lifting mechanism. The body comprises a breathing circuit and an adapter for connecting the carbon dioxide absorbent canister with the breathing circuit. The adapter is located at or near the bottom of the body. The lifting member comprises a base portion, a positioning portion beneath the adapter, and a connecting portion. The lifting mechanism has a force receiving portion and a force applying portion and which actuates the lifting member. Actuating the handle in the first direction causes the canister to be connected to the breathing circuit and to close the breathing circuit bypass. Turning the handle in a second direction actuates the canister to enable replacement of the canister and to cause the breathing bypass to open. The process can be achieved simply with one hand.

20 Claims, 8 Drawing Sheets

FOREIGN PATENT DOCUMENTS

JP    11342206    12/1999

OTHER PUBLICATIONS

Li et al. "Research on Cylindrical Cam Automatic Reversing Mechanism for Two-way Plow" 2000; 4 pages.

Zhao et al. "Application of Electric-Controlled Raise Scaffold and Formwork Integration Technology" Architecture Technology, 2004; vol. 35, No. 8, pp. 568-573.

English Abstract for JP11342206, published Dec. 1999.
English Abstract for De4108383, published Sep. 1992.

* cited by examiner

US 7,964,024 B2

APPARATUS FOR INSTALLING OR UNINSTALLING CARBON DIOXIDE ABSORBENT CANISTER

CROSS-REFERENCE TO RELATED APPLICATION

This application claims the benefit under Title 53, United States Code, §119(a)-(d) or §365(b) from Chinese Patent Application No. 200710076832.1 which is filed on Aug. 31, 2007 into State Intellectual Property Office of the People's Republic of China.

FIELD OF THE INVENTION

Various embodiments of the invention relates to an installation apparatus for a carbon dioxide absorbent canister.

BACKGROUND OF THE INVENTION

In a breathing system of a conventional anesthesia machine, a carbon dioxide ($CO_2$) absorbent is used to absorb the $CO_2$ exhaled by the patient. During this process, the $CO_2$ absorbent becomes gradually inactive and possibly needs replacement during a surgery or between surgeries by, for example, replacing the container which is filled with the $CO_2$ absorbent, i.e., the carbon dioxide absorbent canister. The process of replacing the $CO_2$ absorbent canister depends, in part, on its installation method. Currently, there are primarily four ways to install the $CO_2$ absorbent canister as described below.

(1) A rotary shaft is provided at the installation position of the $CO_2$ absorbent canister of an anesthesia machine. The $CO_2$ absorbent canister is connected to a breathing circuit by engaging the lip of the $CO_2$ absorbent canister with a structure or mechanism in the anesthesia machine, which corresponding to lip of the $CO_2$ absorbent canister, and rotating the $CO_2$ absorbent canister (during this process a breathing gas bypass valve also can be closed simultaneously). After that the canister is fastened by an elastic lock catch, thereby the assembling is completed. A Europe patent of EP 1712246 published on Oct. 18, 2006 describes such an installation structure.

(2) Two vertical sliding bars are provided at the installation position of the $CO_2$ absorbent canister of an anesthesia machine. A tray plate capable of moving up and down along the sliding bar is disposed at the bottom, beneath which a handle to be used by an operator is provided. The operator uses a cam at the back end of the handle to move the tray plate up and down along the sliding bar. The $CO_2$ absorbent canister is, when installed, placed on the tray plate, and then the installation process is completed by means of movement of the tray plate. When in need, the breathing gas bypass valve can be closed by means of the movement.

(3) At the installation position of the $CO_2$ absorbent canister of an anesthesia machine it is provided with a rotating structure. The operator holds the $CO_2$ absorbent canister for rotatably lifting/lowering it by means of a design corresponding to the canister lip, so as to install/uninstall the $CO_2$ absorbent canister and connect the breathing circuit. Also the breathing gas bypass valve can be opened or closed by means of such a motion. This kind of installation structure is disclosed by a Chinese patent published on Aug. 4, 1999 with a publication No. 2331369Y.

(4) Two left and right installation mechanisms are provided at the installation position of the $CO_2$ absorbent canister of an anesthesia machine. Each installation mechanism has a chute. The $CO_2$ absorbent canister can be pushed into the installation mechanism along said two chutes. The operator may lift the $CO_2$ absorbent canister to bring the left and right installation mechanisms rising. The $CO_2$ absorbent canister is fastened via an elastic lock catch inside the installation mechanisms. At the same time, the breathing gas bypass valve is closed so that the $CO_2$ absorbent canister is installed. Upon the pressing on the elastic lock catch, both the left and right installation mechanisms and the $CO_2$ absorbent canister are lowed, and the breathing gas bypass valve is opened at the same time. Here, the operator can remove the $CO_2$ absorbent canister along the chute so as to replace it.

However, the preceding four solutions all have their own disadvantages:

(1) With respect to the first solution, when installing the $CO_2$ absorbent canister, the operator needs to grip the $CO_2$ absorbent canister and rotate it along the rotary shaft against the elastic force of the elastic lock catch. This is continued until the $CO_2$ absorbent canister is tightly locked. During this process, the operator needs to hold the $CO_2$ absorbent canister all the time to overcome its gravity. If the operator loosens the $CO_2$ absorbent canister when it is not tightly locked, the canister shall fall onto the ground. Therefore, the operability of this installation method is poor.

(2) With respect to the second solution, although it is convenient for the operation, the whole mechanism is very complicated and has a huge size, not presenting a compact structure. Moreover, it is not easy to assemble the two sliding bars, and they are not easy to be produced and maintained.

(3) With respect to the third solution, the operator, when installing and uninstalling the $CO_2$ absorbent canister, needs to closely hold the $CO_2$ absorbent canister all the time to overcome its gravity. Also, there is a risk of the $CO_2$ absorbent canister falling onto the ground when the operator looses his hand without tightly cocked the canister.

(4) With respect to the fourth solution, there are two respective steps of placing the $CO_2$ absorbent canister and connecting the breathing circuit, so that the problem of falling due to the incorrect placement and gravity can be solved. However, the operator needs to lift the $CO_2$ absorbent canister when connecting the breathing circuit, thereby the operation is not very convenient.

SUMMARY OF THE INVENTION

One of the technical problems to be solved by some embodiments of the invention is to overcome the disadvantages of the prior art and provide an apparatus for installing or uninstalling a carbon dioxide absorbent canister, which is easy to be operated and has a compact structure.

To solve this technical problem, some embodiments provide apparatus for installing or uninstalling a carbon dioxide absorbent canister which comprises a body, a lifting member, and a lifting mechanism. In some embodiments, the body comprises a breathing circuit and an adapter for connecting the carbon dioxide absorbent canister with the breathing circuit. The adapter is located at or near the bottom of the body in some embodiments. The lifting member is provided with a base portion, a positioning portion for receiving the carbon dioxide absorbent canister, and a connecting portion for connecting the base portion to the positioning member in some embodiments. The positioning portion is located below the adapter, and the lifting mechanism is located on or attached to the body and above the positioning portion in some embodiments. The lifting mechanism comprises a force receiving portion for receiving a power input and a force applying portion for outputting the power. The force applying portion supports the base portion of the lifting member and drives the lifting member to lift or lower in some embodiments.

A chute is provided on or attached to the positioning portion of the lifting member in some embodiments.

In some embodiments, there are two connecting portions and two positioning portions. In some embodiments, the two connecting portions are located on opposed ends of the base portion, and the chutes of the two positioning portions are substantially parallel to each other. One of ordinary skill in the art would know and understand that the chutes of the two positioning portions are substantially parallel to each other due to manufacturing tolerances, clearance or allowance as designed, and/or combination thereof.

In some embodiments, the lifting mechanism comprises a handle, a rotary shaft which is located on or attached to the body, and a cam which is attached on the rotary shaft. The handle is attached to one end of the rotary shaft in some embodiments. The handle comprises the force receiving portion, and the cam comprises the force applying portion.

The body comprises a seat, an upper lid, and a lower lid in some embodiments. The seat comprises an inner circumferential wall and an outer circumferential wall in some embodiments. The inner circumferential wall defines an installation chamber, and a radial installation plate is attached to the inner circumferential wall in some embodiments. In some embodiments, the installation chamber defines a through aperture at or around an axis of the installation chamber. Both the upper and lower lids are located within the installation chamber and attached to the installation plate, thereby a breathing circuit is formed between the upper lid and the lower lid in some embodiments. The adapter is provided on or attached to the lower lid in some embodiments. The rotary shaft rests on the upper lid in some embodiments. The cam is fixed to a portion of the rotary shaft that extends into the installation chamber, and the handle is mounted on or attached to a portion of the rotary shaft that extends beyond the upper lid in some embodiments.

In some embodiments, the handle is rotatably mounted on or attached to the rotary shaft by a bearing shaft, the axis of the bearing shaft is substantially perpendicular to the axis of the rotary shaft, and the outer circumferential wall of the seat comprises two retaining edges. One of ordinary skill in the art would know and understand that the chutes of the two positioning portions are substantially parallel to each other due to manufacturing tolerances, clearance or allowance as designed, and/or combination thereof.

The installation plate is provided with upstanding guide posts in some embodiments. The base portion of the lifting member is located within the installation chamber of the seat and encases the guide posts.

In some embodiments, the body further comprises a first bypass valve for forming a breathing bypass.

In some embodiments, the body further comprises a second bypass valve for controlling the connection and disconnection between the breathing circuit and the adapter or the opening or closing of the passage between the breathing circuit and the adapter. In these embodiments, the movement of the second bypass valve is associated with the movement of the first bypass valve. In some embodiments, the movement of the second bypass valve is associated with the movement of the first bypass valve when the movement of the second bypass valve causes the movement of the first bypass valve or vice versa.

In some embodiments, each of the first and second bypass valves comprises a valve chamber, a valve gate, and a valve rod. In some embodiments, the valve gate matches against an opening of the valve chamber and is attached to the valve rod which is oriented in a substantially vertical direction, and the bottoms or the lower portions of the two valve rods are attached to a tray plate.

The advantages of the invention comprises: (1) the entire process of replacing the $CO_2$ absorbent canister comprises two actions. In some embodiments, the operator turns or manipulates the handle (31) to actuate the handle from a position where the handle is oriented in a substantially horizontal direction to another position where the handle is oriented in a substantially vertical direction. The turning of the handle causes the rotary shaft (32) and the cam (33) to rotate to lower the lifting member (2) and the carbon dioxide absorbent canister (4). In some embodiments, the operator then removes the carbon absorbent canister (4) by disengaging the slide rails (411) from the chutes (231). (2) the lifting mechanism is located above the $CO_2$ absorbent canister such that the device is compact and easy to assemble and operate in some embodiments.

BRIEF DESCRIPTION OF THE DRAWINGS

The drawings illustrate the design and utility of various embodiments of the invention, in which similar elements are referred to by common reference numerals. In order to better appreciate how advantages and objects of various embodiments of the inventions are obtained, a more particular description of various embodiments of the inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION

Figure 1:
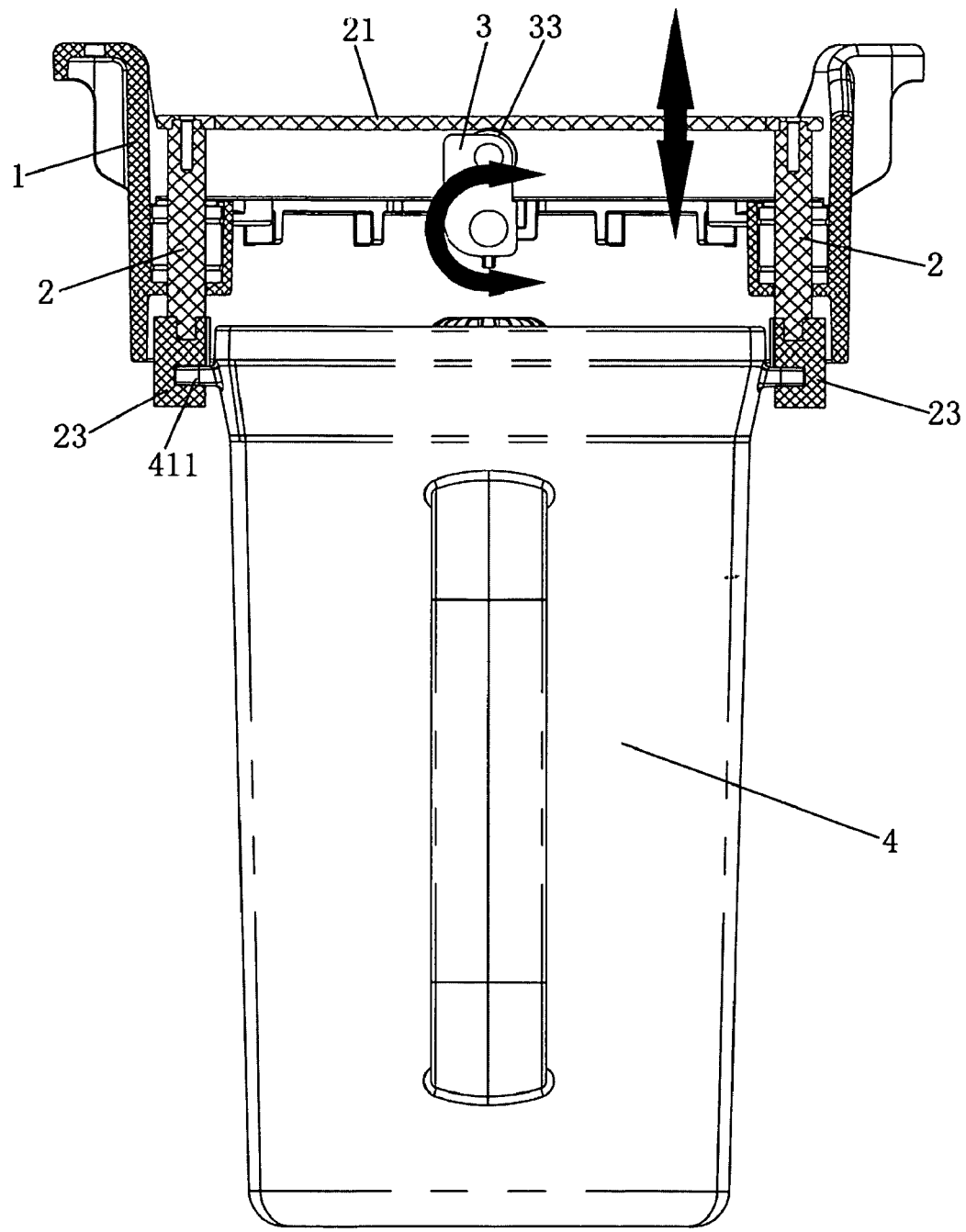
FIG. 1 illustrates a structural schematic view of an apparatus for installing or uninstalling a carbon dioxide ($CO_2$) absorbent canister according to an embodiment.
Figure 2:
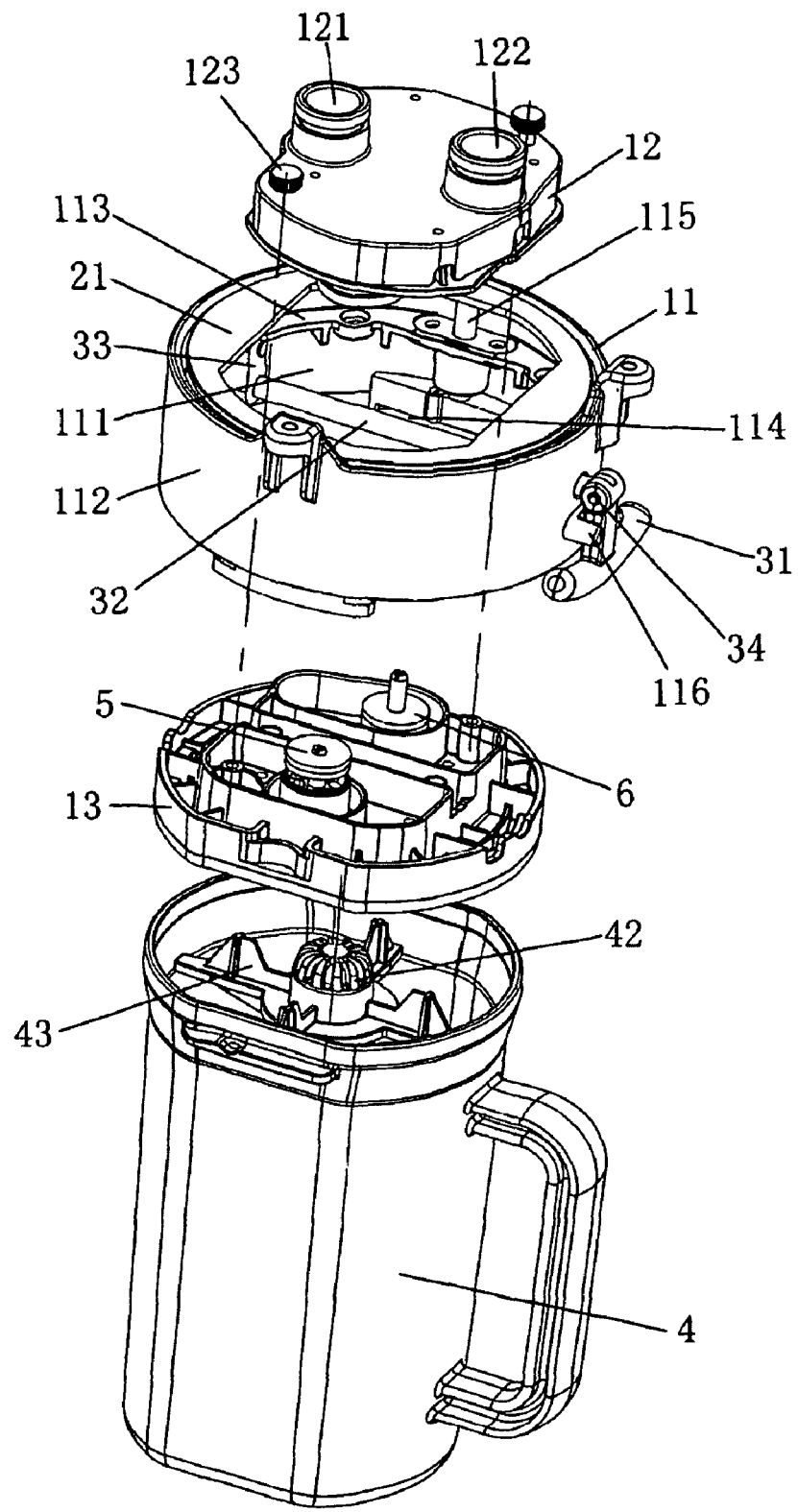
FIG. 2 illustrates a perspective exploded view of the apparatus for installing or uninstalling a $CO_2$ absorbent canister according to the embodiment.
Figure 3:
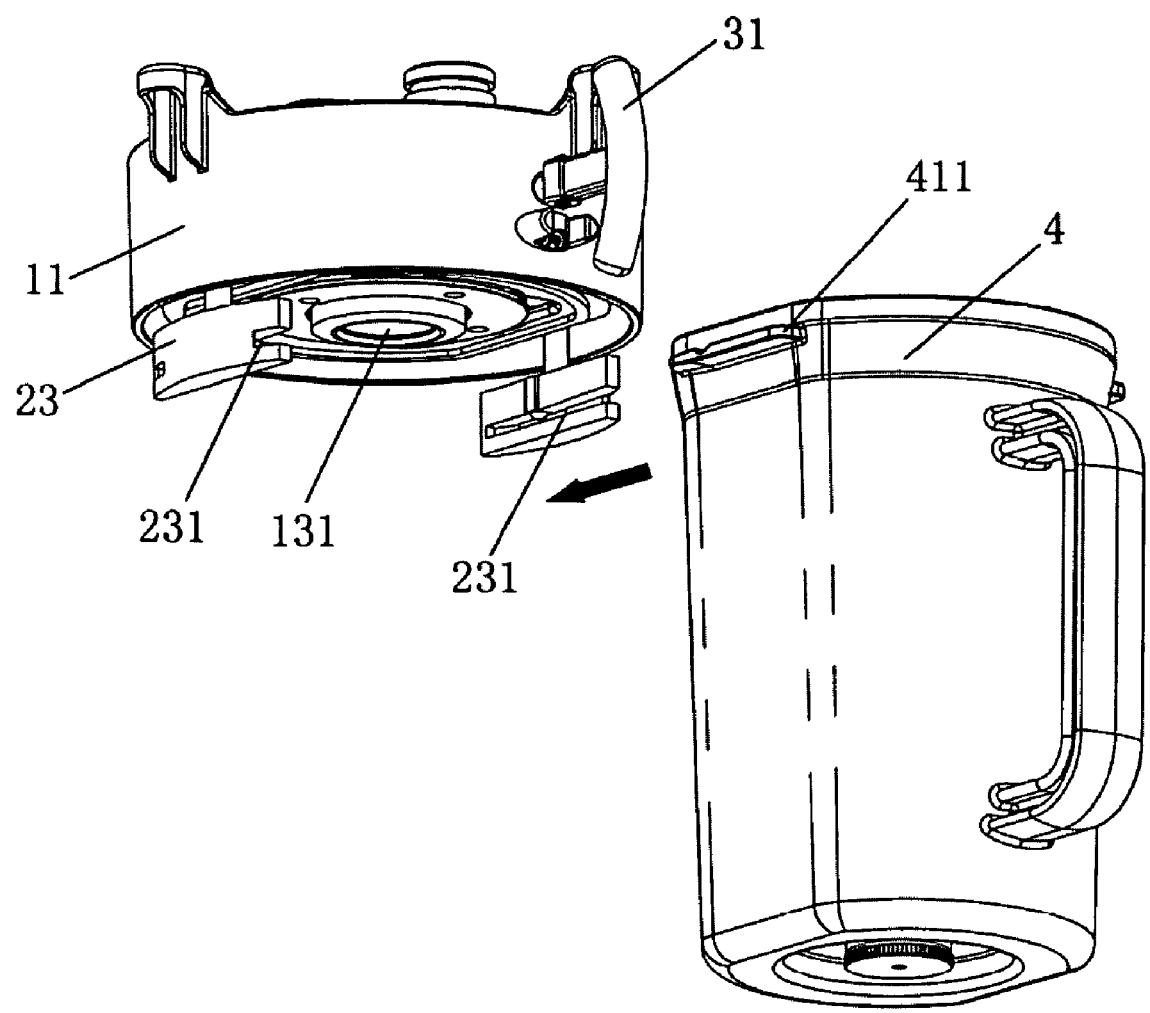
FIG. 3 illustrates a view of the arrangement of the body and the $CO_2$ absorbent canister according to the embodiment before final assembly.
Figure 4:
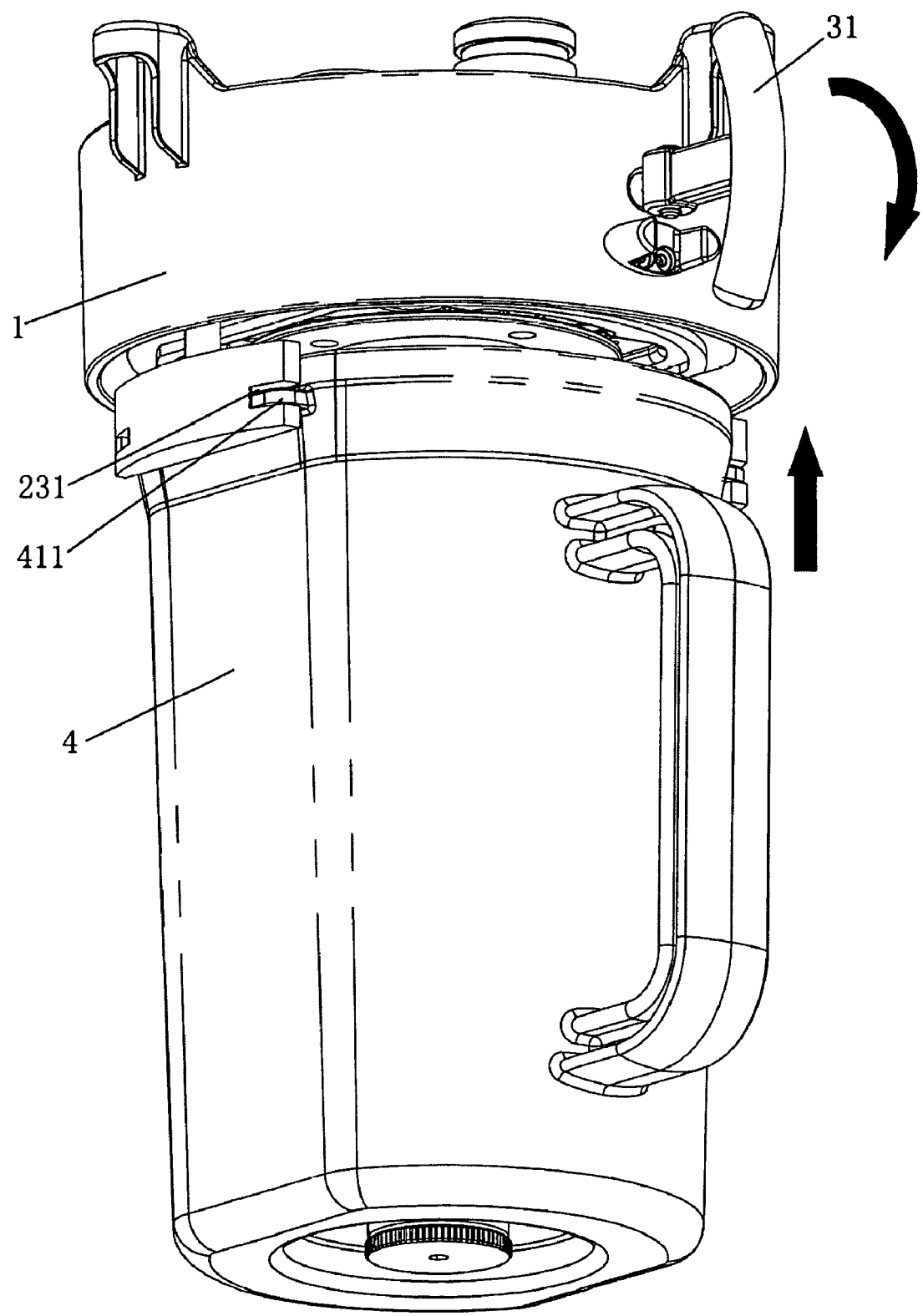
FIGS. 4 to 6 illustrate the assembly process of the body and the $CO_2$ absorbent canister by respectively showing three states of lifting the $CO_2$ absorbent canister, lifting the $CO_2$ absorbent canister in place, and placing the handle in place.
Figure 5:
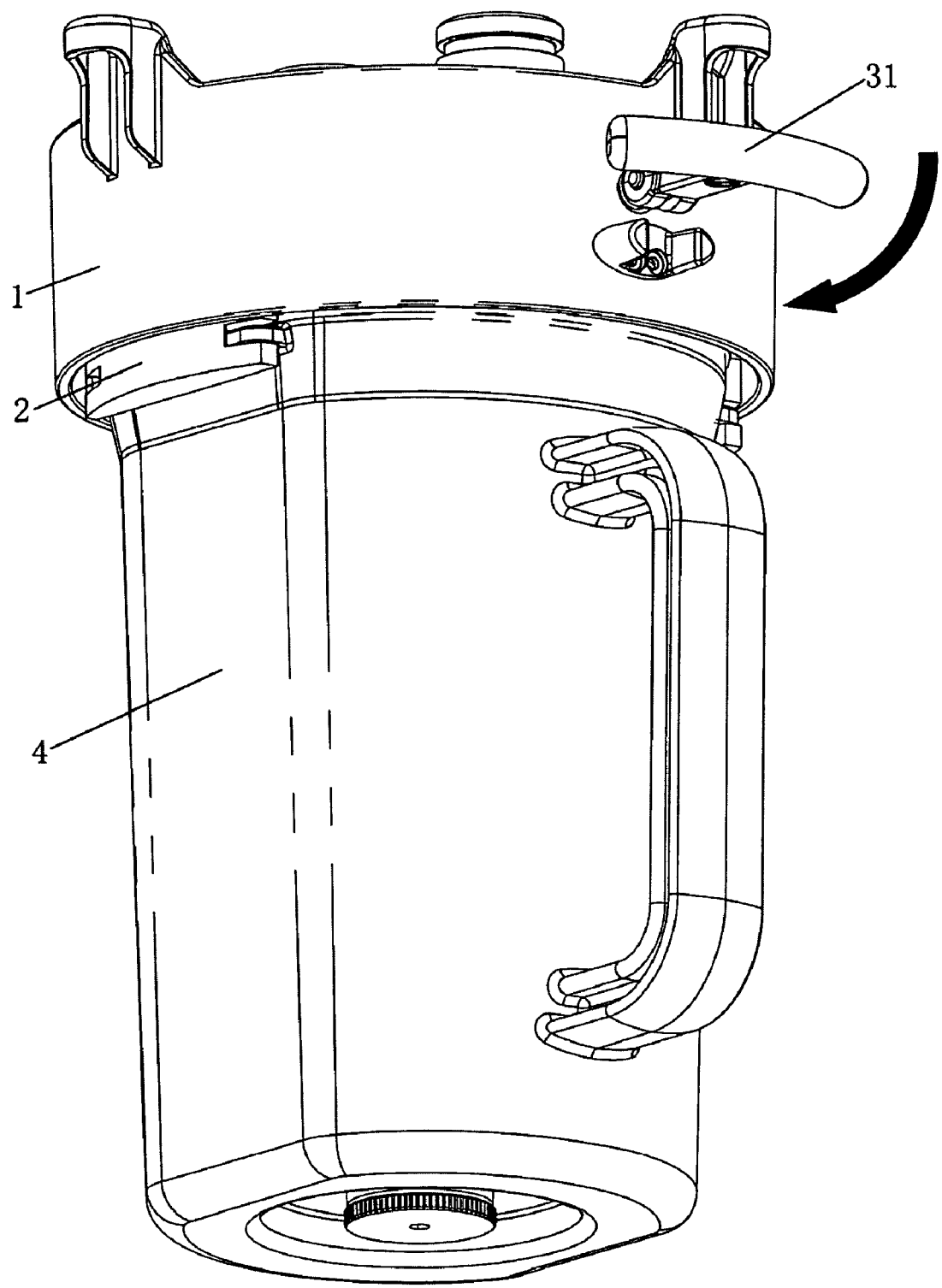
Figure 6:
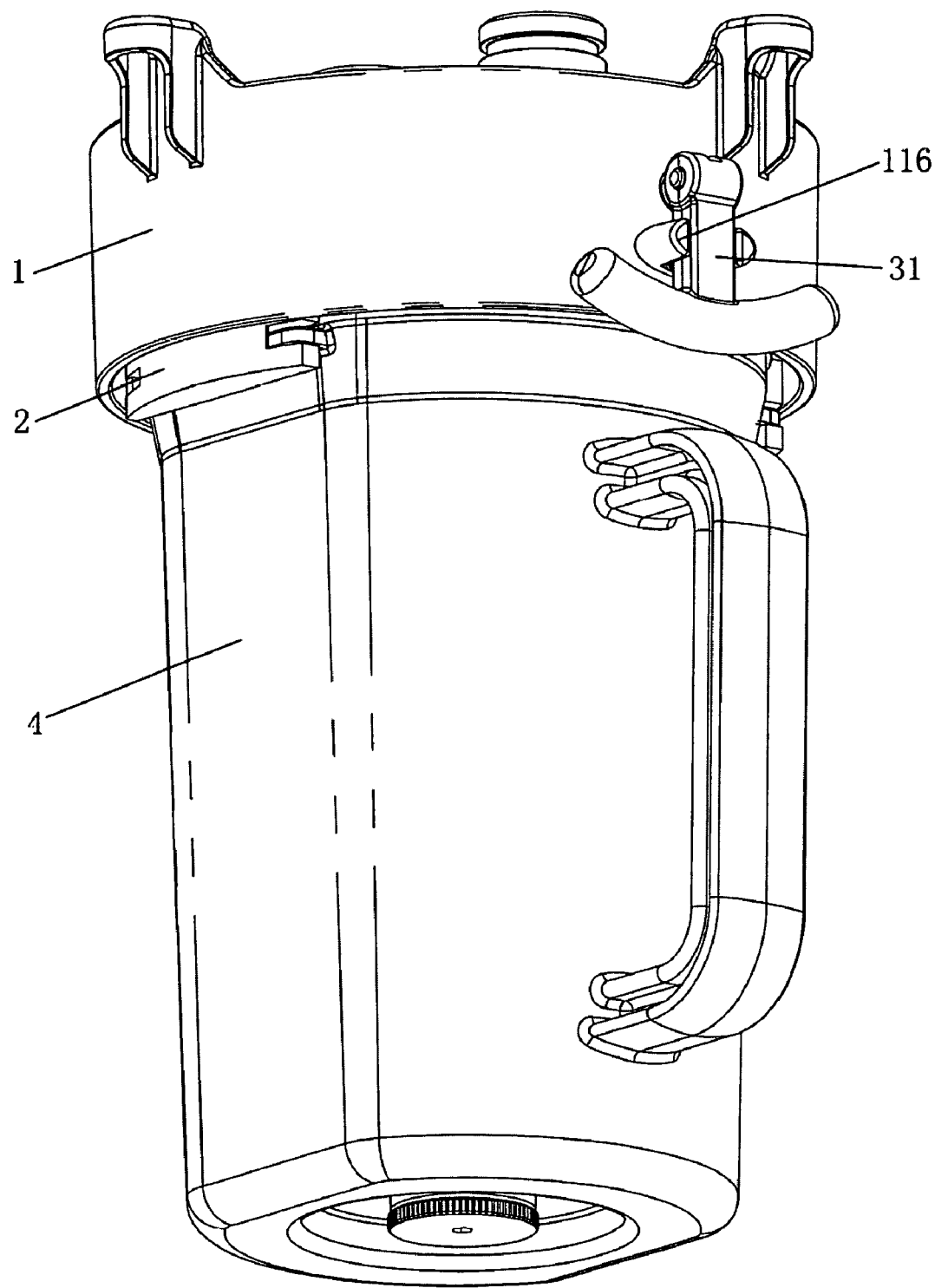
Figure 7:
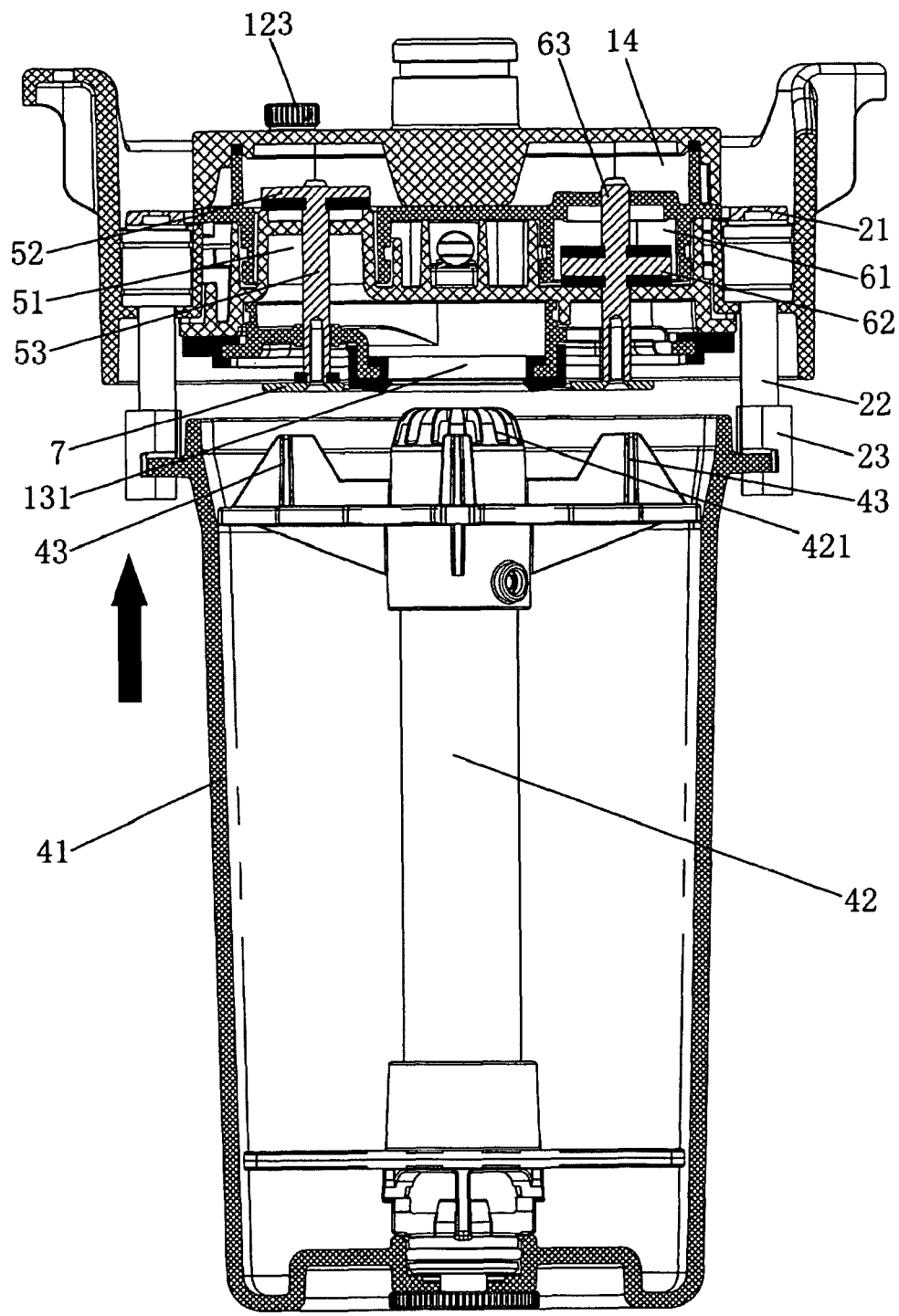
FIG. 7 illustrates a sectional view of the $CO_2$ absorbent canister being lifted.
Figure 8:
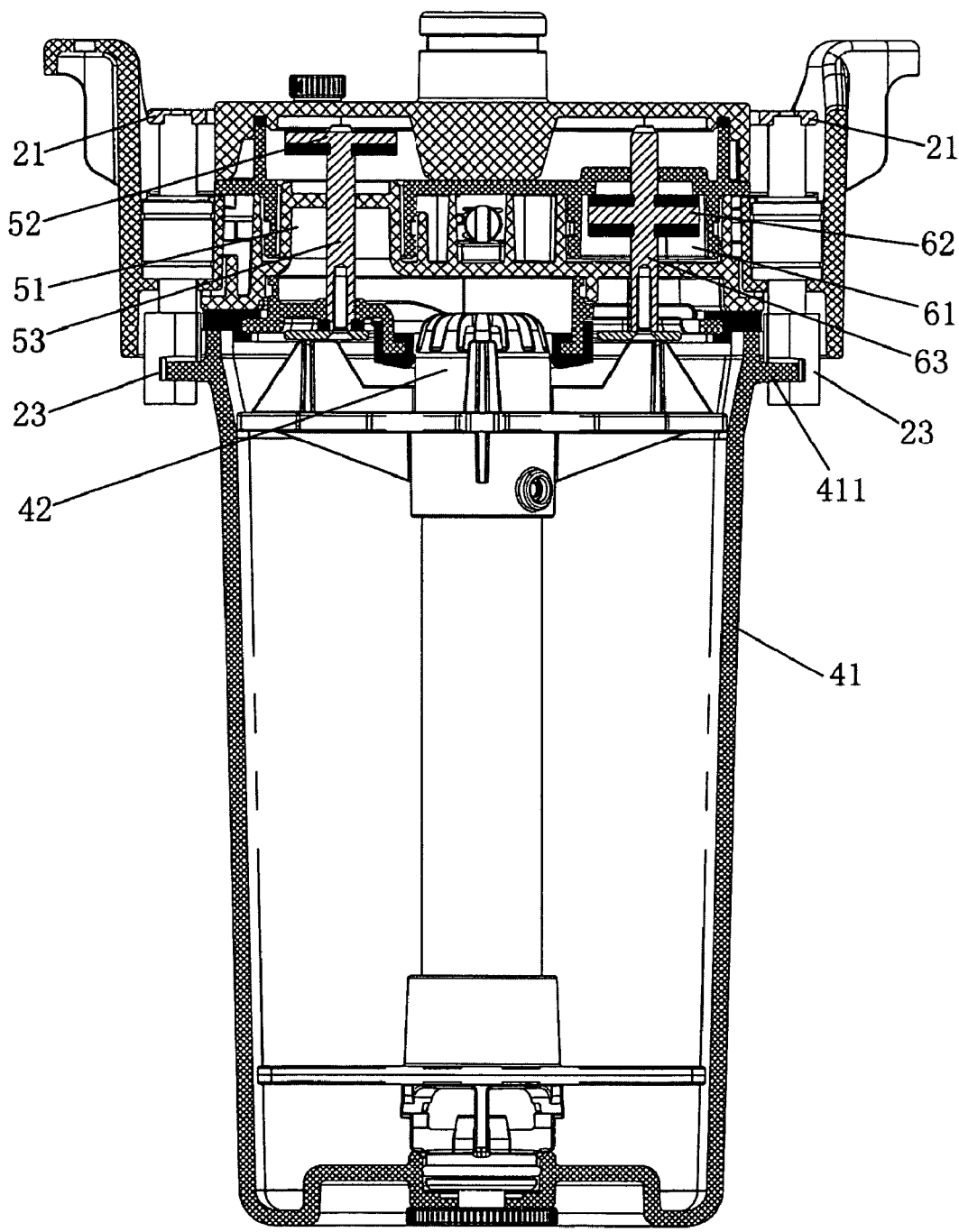
FIG. 8 illustrates a cross-sectional view of the $CO_2$ absorbent canister lifted.

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings. As shown in FIGS. 1 to 8, an apparatus for installing a $CO_2$ absorbent canister according to several embodiments of the invention for installing a $CO_2$ absorbent canister 4 includes a body 1, a lifting member 2, a lifting mechanism 3, a first bypass valve 6, and a second bypass valve 5.

In some embodiments, the body 1 comprises a seat 11, an upper lid 12, and a lower lid 13. The seat 11 has an inner circumferential wall 111 and an outer circumferential wall 112. The inner circumferential wall 111 defines an installation chamber 114. An installation plate 113 extends from the inner circumferential wall 111 along a radial direction. The upper lid 12 has a breathing gas inlet 121 through which the gas from an anesthesia machine is fed and a breathing gas outlet 122 through which the gas is exhausted. Both the first bypass valve 6 and the second bypass valve 5 are located on or attached to the lower lid 13. The bottom of the lower lid 13 is provided with an adapter 131 for mounting the $CO_2$ absorbent canister 4.

In some embodiment, the lifting member 2 has a π shape and is fitted within the installation chamber 114 of the seat. The lifting member 2 comprises a base portion 21, two connecting portions 22, and two positioning portions 23. In some embodiments, the base portion 21 assumes the shape of a plate and defines a through aperture at about its central axis. In these embodiments, the base portion 21 is located above the installation plate 113 of the seat 11. In some embodiments, the tops of the two connecting portions 22 are fixed at two opposite ends of the base portion 21 respectively, while the bottoms or the lower portions of the two connecting portions 22 are connected or attached to the two positioning portions 23 respectively. In several embodiments, each of the two positioning portions 23 has a chute 231 into which the $CO_2$ absorbent canister 4 is fitted.

Both of the two chutes 231 extend substantially horizontally and are substantially parallel to each other. In some embodiments, the two chutes 231 extend substantially horizontally and are substantially parallel to each other due to manufacturing tolerances, clearance, allowance, and/or combination thereof. In some embodiments, the lifting mechanism 3 comprises a handle 31, a rotary shaft 32, and a cam 33. The rotary shaft 32 is substantially horizontally inserted into the seat 11 and has a first portion extending into the installation chamber 114 and a second portion located outside of the seat. The cam 33 is fixed on the first portion in some embodiments.

The handle 31 is mounted on the second portion. The base portion 21 of the lifting member 2 rests on the cam 33. The handle 31 is rotatably mounted on or to the rotary shaft 32 by a bearing shaft 34. In some embodiments, the axis of the bearing shaft 34 is substantially orthogonal to the axis of the rotary shaft 32 such that the handle 31 can be rotated or spun not only about the axis of the rotary shaft 32 but also about the axis of the bearing shaft 34. The handle 31, when being rotated or spun, rotatably drives the rotary shaft 32 and the cam 33 which fixed on the rotary shaft 32. The lifting member 2 is raised or lowered in a substantially vertical direction as the cam 33 rotates or spins so that the movements of the lifting member 2 and the lifting mechanism 3 are associated with each other. In some embodiments, a retainer which comprises two retaining edges 116 is connected to the outer circumferential wall 112 or is integrally formed with the outer circumferential wall 112 of the seat 11 with manufacturing techniques which comprise machining, bonding, welding, or brazing. In some embodiments, the retainer defines two retaining edges 116 in order to prevent the rotary shaft 32 from deviating or moving away from a designated position after rotating or moving to the designated position. Moreover, in order to guide the linear motion of the lifting member, two guide posts 115 are fixed in a substantially vertical direction on the installation plate 113 of the seat in some embodiments. In some embodiments, the base portion 21 of the lifting member rests on the cam 33 and encases the two guide posts 115. In some embodiments, the axis of the bearing shaft is substantially orthogonal to the axis of the rotary shaft 32 due to manufacturing tolerances, clearance, allowance, and combination thereof. In some embodiments, the lifting member 2 is raised or lowered in a substantially vertical direction due to manufacturing tolerances, clearance, allowance, and combination thereof. In some embodiments, the two guide posts 115 are fixed in a substantially vertical direction due to manufacturing tolerances, clearance, allowance, and combination thereof. In some embodiments, the second bypass valve 5 has a second valve chamber 51, a second valve rod 53 which is oriented in a substantially vertical direction, and a second valve gate 52 mounted on the top or an upper portion of the second valve rod 53. The first bypass valve 6 comprises a first valve chamber 61, a first valve rod 63 which is oriented in a substantially vertical direction, and a first valve gate 62 mounted at about the middle of the first valve rod 63. The bottoms or lower portions of the second valve rod 53 and the first valve rod 63 both are fixed on a tray plate 7 that is oriented in a substantially horizontal direction in some embodiments. In some embodiments, the second valve rod 53 is oriented in a substantially vertical direction due to manufacturing tolerances, clearance, allowance, and combination thereof. In some embodiments, the first valve rod 63 is oriented in a substantially vertical direction due to manufacturing tolerances, clearance, allowance, and combination thereof. Similarly, in some embodiments, the tray plate 7 is oriented in a substantially horizontal direction due to manufacturing tolerances, clearance, allowance, and combination thereof.

In various embodiments, the $CO_2$ absorbent canister 4 has a hollow casing 41 for receiving and/or accommodating the $CO_2$ absorbent, such as soda lime, and a hollow core 42 which is located at or near the central portion of the casing 41. In some embodiments, the outer wall of the casing 41 defines or is provided with two slide rails 411 which respectively correspond to and function with the two chutes 231 of the lifting member 2. The lower part of the core 42 is fixed or attached to the casing 41. The upper part of the core 42 is provided with four supporting frames 43, and the top of the core 42 has holes 421 facilitating for gas flow. In some embodiments, the supporting frames 43 assumes a shape of a cross.

In some embodiments, when installing the body, both the upper lid 12 and the lower lid 13 are fitted in the installation chamber 114 of the seat 11 with the installation plate 113 of the seat 11 clamped or secured by the upper lid 12 and the lower lid 13 from the upper and lower sides respectively. In some embodiments, the upper lid 12 and the lower lid 13 are fastened or secured by fasteners 123 or other devices serving similar purposes, such that the upper lid 12, the seat 11, and the lower lid 13 may be connected together, and thereby a breathing circuit 14 is formed between the upper lid 12 and the lower lid 13. One of ordinary skill in the art shall also appreciate that any two portions of the apparatus as disclosed herein that may be secured together with fasteners or similar devices to form a separable assembly may also be manufactured as a single piece or may be joined as an inseparable part by various joining techniques comprising various welding, brazing, or bonding techniques. In some embodiments, after the apparatus for installing or uninstalling the carbon dioxide absorbent canister is assembled, both of the two positioning portions 23 of the lifting member 2 are located beneath the adapter 131 of the lower lid 13, while the lifting mechanism 3 is located above the positioning portions 23.

In order to install the $CO_2$ absorbent canister 4 in some embodiments, an operator may engage the carbon dioxide absorbent canister 4 with the lifting member 2 by pushing the slide rails 411 of the $CO_2$ absorbent canister 4 into the chutes 231 of the position portions 23 such that the carbon dioxide absorbent canister 4 is attached to the position portion 23 of the lifting member 2 along these chutes, and then the operator may release his or her hand(s) as the lifting member 2 carries at least some of weight of and support the carbon dioxide absorbent canister 4. In some other embodiments, an operator may achieve the same using automated or semi-automated mechanisms for at least some of the aforementioned components. At or around this time or shortly after, the core 42 of the $CO_2$ absorbent canister 4 is not engaged with the adapter 131 of the lower lid 13 in these embodiments. The second valve rod 53 is located in or near the lowermost or a lower position, and the second valve gate 52 closes the opening of the second valve chamber 51 such that the breathing circuit 14 is not in connection with the adapter 131 and the gas may not leak into the atmosphere in some embodiments.

At or around the same time or shortly after, the first bypass valve 6 is switched to a first position to form a breathing circuit bypass in some embodiments. In these embodiments, the desired gas(es) from the breathing system of the anesthesia machine is introduced to the patient through the breathing gas inlet 121, the first valve chamber 61, and then the breathing gas outlet 122 so that the anesthesia machine can be operated normally even when the $CO_2$ absorbent canister 4 is in a process of being replaced. In these embodiments, the first bypass valve 6 is switched to a second position after the completion of the replacement of the carbon dioxide absorbent canister 4 such that the desired gas(es) may be introduced to the patient from through the breathing gas inlet 121, the first bypass valve chamber 61, the carbon dioxide absorbent canister 4, the second bypass valve 5, and then the outlet 122.

In some embodiments, the first bypass valve 6 comprises a three-way valve with three ports which comprise the open position, the first position, and the second position. In some embodiments, the first bypass valve 6 comprises a multiple-way valve with more than three ports. In some embodiments, the first bypass valve 6 comprises a two-way valve with two ports which comprise the open position and the closed position such that the breathing system temporarily stops flowing the desired gas during the process of replacing the carbon dioxide absorbent canister 4. Some embodiments may comprise multiple valves, each with equal or different number of ports, to achieve similar or identical purposes as the use of a three-way or multiple-way first bypass valve 6 would achieve.

In some embodiments, the handle 31 is rotated, turned, or otherwise manipulated manually, automatically, or semi-automatically to cause the rotary shaft 32 and the cam 33 to rotate and raise or lower the cam 33, and the cam 33 drives the lifting member 2 to lift the $CO_2$ absorbent canister 4 in a substantially vertical direction. In some embodiments, the handle is rotated, turned, or otherwise manipulated manually, automatically, or semi-automatically from a substantially vertical orientation to another orientation in a clockwise or counter-clockwise direction to cause the rotary shaft 32 and the cam to rotate and thus causes to actuate the lifting member 2 to raise the carbon dioxide absorbent canister 4. In some embodiments, the cam 33 drives the lifting member 2 to lift the CO2 absorbent canister 4 in a substantially vertical direction due to manufacturing tolerances, allowance, or clearance. In some embodiments, the operator needs to support or carry at least part of the weight of the carbon dioxide absorbent canister only during engaging or disengaging the lifting member 2.

When the handle 31 is rotated or turned to a position, such as a horizontal or substantially horizontal orientation in some embodiments, the $CO_2$ absorbent canister 4 is inserted into the adapter 131 of the lower lid 13 to connect to the breathing circuit 14 of the body. During this lifting process in some embodiments, the supporting frames 43 of the $CO_2$ absorbent canister 4 moves the tray plate 7 up to drive the second valve rod 53 and the first valve rod 63 to lift in a substantially vertical direction. After the handle is rotated to the position, the second valve gate 52 opens to cause the breathing circuit 14 to be in connection with the adapter 131 and thereby allows the gas from the breathing system of the anesthesia machine to flow through the breathing gas inlet 121, the $CO_2$ absorbent canister 4, and the breathing gas outlet 122. At around the same time or shortly thereafter, the first valve gate 62 of the first bypass valve 6 completely or partially closes the opening of the first valve chamber 61, namely closing the breathing circuit bypass. After the handle 31 is rotated to a horizontal or a substantially horizontal position, the handle 31 may be pulled downwards to be positioned between the two retaining edges 116 to prevent the rotary shaft 32 from moving or straying out of the designated position between the two retaining edges 116. The operator may uninstall the $CO_2$ absorbent canister 4 by reversing the above steps.

In some embodiments, the installation of the $CO_2$ absorbent canister 4 may be categorized into two actions. In some embodiments, the lifting member 2 with the chutes 231 at least partially carries the weight of the $CO_2$ absorbent canister 4. The handle may be turned or actuated in a first direction to drive the rotary shaft 32 and therefore the cam 33 to lift the lifting member 2 and the $CO_2$ absorbent canister 4 to connect the $CO_2$ absorbent canister 4 to the breathing circuit 14 and close the breathing circuit bypass. In some embodiments, turning or actuating the handle 31 in a second direction drives the rotary shaft 32 and therefore the cam 33 to lower the lifting member 2 and the $CO_2$ absorbent canister 4. In these embodiments, the breathing circuit bypass is opened. Then the operator may remove the $CO_2$ absorbent canister 4 from the chutes 33 of lifting member 2 to replace the $CO_2$ absorbent.

In some embodiments, it is known to one of ordinary skill in the art that the lifting mechanism may be replaced by a lever mechanism or other up and down sliding mechanisms so long as these mechanisms achieve similar or identical purpose of moving or actuating the $CO_2$ absorbent canister 4 up and down. In some embodiments, the bypass valve may not be needed for serving the intended purpose of installing and/or uninstalling the $CO_2$ absorbent canister 4.

Other aspects and features of the invention will be evident from reading the following detailed description of the preferred embodiments, which are intended to illustrate, not limit, the invention. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

The invention claimed is:

1. An apparatus for installing a carbon dioxide absorbent canister, the apparatus comprising:
   a body comprising a breathing circuit, a first bypass valve configured for a breathing bypass, and an adapter for connecting the carbon dioxide absorbent canister to the breathing circuit, wherein
      the adapter is located at or near the bottom of the body; and
   a lifting member and a lifting mechanism, wherein
      the lifting member comprises:
         a base portion;
         a positioning portion for attaching the carbon dioxide absorbent canister; and
         a connecting portion for connecting the base portion to the positioning portion, in which the positioning portion is located beneath the adapter, and the lifting mechanism is disposed on the body and above the positioning portion, and
      the lifting mechanism comprises:
         a force receiving portion for receiving a power input; and
         a force applying portion for outputting power, wherein the force applying portion supports the base portion and causes the lifting member to move.

2. The apparatus of claim 1, wherein the positioning portion of the lifting member comprises a chute.

3. The apparatus of claim 2, wherein
   the lifting member comprises a second connecting portion and a second positioning portion,
   the second positioning portion comprises a second chute,
   the connecting portion and the second connecting portion are located at opposed ends of the base portion, and
   the chute and the second chute are substantially parallel to each other.

4. The apparatus of claim 1, wherein the lifting mechanism comprises:
   a handle;
   a rotary shaft disposed on the body; and
   a cam fixed on the rotary shaft, the handle is mounted at or near an end of the rotary shaft, the handle comprises the force receiving portion, and the cam comprises the force applying portion.

5. The apparatus of claim 4, wherein the body further comprises:
   a seat;
   an upper lid; and
   a lower lid, in which the seal comprises an inner circumferential wall and an outer circumferential wall, wherein
      the inner circumferential wall defines an installation chamber,
      a radial installation plate is attached to the inner circumferential wall,
      both the upper and lower lids are located within the installation chamber and are attached to the installation plate,
      a breathing circuit is situated between the upper lid and the lower lid,
      the adapter is attached to or is an inseparable part of the lower lid,
      the rotary shaft rests on the upper lid,
      the cam is attached to a portion of the rotary shaft which extends into the installation chamber, and
      the handle is attached to a portion of the rotary shaft that extends beyond the upper lid.

6. The apparatus of claim 5, wherein the handle is rotatably mounted on the rotary shaft by a bearing shaft, an axis of the bearing shaft is substantially perpendicular to the axis of the rotary shaft, and the outer circumferential wall of the seat comprises two retaining edges.

7. The apparatus claim 5, wherein a guide post is attached to the installation plate, the base portion of the lifting member is situated within the installation chamber and encases the guide post.

8. The apparatus of claim 1, wherein the body comprises the first bypass valve for the breathing bypass, and the first bypass valve opens and closes according to movement of the lifting member.

9. The apparatus of claim 8, wherein the body further comprises a second bypass valve for controlling a connection between the breathing circuit and the adapter, a movement of the second bypass valve is associated with a movement of the first bypass valve.

10. The apparatus of claim 9, wherein each of the first and second bypass valves comprises a valve chamber, a valve gate, and a valve rod, wherein the valve gate matches with an opening of the valve chamber and is attached to the valve rod which is oriented in a substantially vertical direction, and a lower portion of the valve rod is attached to a tray plate.

11. The apparatus of claim 1, in which the bypass valve is configured to provide one or more anesthetics through the body during installation or removal of the carbon dioxide absorbent canister.

12. A method for using an apparatus for installing a gas absorbent canister, comprising:
   positioning the gas absorbent canister by using a positioning portion of a lifting member of a gas absorbent installation or removal device, wherein
      the positioning portion is used to attach the gas absorbent canister in the gas absorbent installation or removal device;
   receiving a power input at a force receiving portion of a lifting mechanism;
   installing or removing the gas absorbent canister by outputting a power output at a force applying portion of the lifting mechanism according to the power input, wherein
      the force applying portion is configured to support a base portion of the lift member and causes the lifting member to move, and
      the base portion is connected to the positioning portion by using at least a connecting portion; and
   connecting or disconnecting a breathing bypass by using at least the power output that causes to actuate a first bypass valve of a body of the gas absorbent canister installation or removal device, wherein
      the gas absorbent canister is connected to an adapter of the body of the gas absorbent canister installation or removal device.

13. The method of claim 12, wherein the action of installing or removing the gas absorbent canister comprises:
   moving the gas absorbent canister along at least one chute of the lifting member.

14. The method of claim 12, further comprising:
   positioning the gas absorbent canister by using a second positioning portion of the lifting member of the gas absorbent installation or removal device; and
   connecting the base portion to the second positioning portion by using a second connecting portion.

15. The method of claim 12, in which the action of receiving the power input at the force receiving portion of the lifting mechanism comprises:

actuating a handle of the lifting mechanism to drive a rotary shaft disposed on the body via receiving the power input at the force receiving portion of a cam that comprises the force applying portion and is fixedly attached to the rotary shaft.

16. The method of claim 12, further comprising:
actuating a handle of the lifting mechanism to drive a rotary shaft disposed on the body via receiving the power input at the force receiving portion of a cam that comprises the force applying portion and is fixedly attached to the rotary shaft.

17. The method of claim 12, further comprising:
actuating the first bypass valve to connect or disconnect the breathing bypass by actuating the lifting mechanism.

18. The method of claim 12, further comprising:
associating the first bypass valve with a second bypass valve, in which opening or closing of the first bypass valve is associated with opening or closing of the second bypass valve; and opening or closing a connection between the breathing circuit and the adapter of the body by actuating the first bypass valve or the second bypass valve.

19. The method of claim 18, in which the opening or closing of the first bypass valve or the second bypass valve is performed by actuating the lifting member.

20. The method of claim 12, further comprising:
providing or maintaining one or more anesthetics through the body of the gas absorbent canister during installation or removal of the gas absorbent canister.

* * * * *